(12) United States Patent
Fukushima

(10) Patent No.: US 6,579,692 B1
(45) Date of Patent: *Jun. 17, 2003

(54) METHOD OF SCREENING APOPTOSIS INDUCING SUBSTANCES

(75) Inventor: Naoshi Fukushima, Gotemba (JP)

(73) Assignee: Chugai Seiyaku Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,004

(22) PCT Filed: Mar. 6, 1997

(86) PCT No.: PCT/JP97/00702

§ 371 (c)(1),
(2), (4) Date: Sep. 8, 1998

(87) PCT Pub. No.: WO97/32601

PCT Pub. Date: Sep. 12, 1997

(30) Foreign Application Priority Data

Mar. 6, 1996 (JP) ............................................. 8-078182

(51) Int. Cl.⁷ .................................................. C12Q 1/02
(52) U.S. Cl. ............................................ 435/29; 435/4
(58) Field of Search ........................................ 435/4, 29

(56) References Cited

U.S. PATENT DOCUMENTS 5,614,397 A * 3/1997 Welssman et al.

FOREIGN PATENT DOCUMENTS

EP 0 721 015 7/1996
WO WO 95/06748 3/1995

OTHER PUBLICATIONS

Carlos Rosales, et al., The Journal of Immunology, vol. 149, No. 8, pp. 2759–2764, "Expression of the 50–kDa Integrin–Associated Protein on Myeloid Cells and Erythrocytes[1]", Oct. 15, 1992.

Eric Brown, et al., The Journal of Cell Biology, vol. 111, No. 6, pp. 2785–2794, "Integrin–Associated Protein: A 50–kD Plasma Membrane Antigen Physically and Functionally Associated With Integrins", Dec. 1990.

Shoukat Dedhar, Cancer and Metastasis Reviews, vol. 14, pp. 165–172, Integrin Mediated Signal Transduction in Oncogenesis: An Overview, 1995.

* cited by examiner

*Primary Examiner*—Patrick J. Nolan
(74) *Attorney, Agent, or Firm*—Oblon, Spivak, McClelland, Maier & Neustadt, P.C.

(57) ABSTRACT

The present invention provides a method of screening substances having property of causing apoptosis, and relates to a method of screening substances having property of causing apoptosis characterized by using cells which are expressing IAP (Integrin Associated Protein), and the relates to above screening method, wherein the cells used are myeloid cells, and relates to pharmaceutical compositions containing as the active ingredient the substances obtained by the above method, and the present invention makes it possible to differentiate, identify and screen readily and highly efficiently the substances, such as antibodies and the like, that have property of causing apoptosis on myeloid cells by using cells which are expressing IAP while using specific binding reactions of the substances, and the above specific substances thus obtained can be used by virtue of their characteristics as the active ingredient of pharmaceutical compositions such as anticancer agents and medicines for myelocytic leukemia and the like.

12 Claims, 17 Drawing Sheets

Monoclonal Antibody (BMAP-1) Concentration

Assay for BMAP-1 to inhibit NFS-60 cell proliferation

Monoclonal Antibody Assay for GSPST-1 to inhibit the bone marrow transplantation Monoclonal Antibody Assay for BMAP-1 to inhibit the bone marrow transplantation (1)

(2)

Cytotoxicity assay using L-929 cells by TNFα

Cytotoxicity assay using L-929 cells by BMAP-1

BMAP-1 concentration ( /ml)

Proliferation inhibitory action to BMAP-1 cells (Jurkat cells transfected with murine IAP gene)

US 6,579,692 B1

METHOD OF SCREENING APOPTOSIS INDUCING SUBSTANCES

This Application is 35 USC §371 of PCT/JP97/00702, filed Mar. 6, 1997.

1. Technical Field

The present invention relates to a method of screening substances having property of causing apoptosis and the like, in particular, relates to a novel screening method which makes it possible to screen readily and highly efficiently the substances, such as monoclonal antibodies and the like, that have property of causing apoptosis on myeloid cells by using cells which are expressing IAP (Integrin Associated Protein), and relates to the substances having property of causing apoptosis obtained by the above screening method, pharmaceutical compositions containing as the active ingredient the above substances, and relates to substances having property of causing apoptosis which have a specific binding activity to IAP, pharmaceutical compositions containing as the active ingredient the above substances.

2. Background Art

Granulocyte colony-stimulating factors, for example, recombinant granulocyte colony-stimulating factors (rG-CSF), have been known primarily as humoral factors to stimulate the differentiation and proliferation of granulocyte cells, and it has been reported in an experiment upon mice in vivo that the administration of rG-CSF enhances the hematopoiesis of the bone marrow and in addition causes remarkable extramedullary hematopoiesis in the spleen to proliferate hematopoietic stem cells and all hematopoietic precursor cells in the spleen. And it has been thought as extramedullary hematopoietic mechanism in the spleen that hematopoiesis occurs due to a splenic hematopoietic microenvironment modifications according to the stimulation of rG-CSF to enhance hematopoietic potential.

Hence, the present inventors have noted splenic stromal cells administered rG-CSF with a view to clarifying the hematopoietic potential in the spleen, and established a hematopoietic stromal cell line (CF-1 cells) from the spleen of a mouse administered rG-CSF with a view to attempting the analysis of the enhancement of the hematopoietic potential by stromal cells with rG-CSF, and examined the potential effect on hematopoiesis using the hematopoietic stromal cells, and as a result, colony-stimulating activities in vitro and potency supportive of hematopoietic stem cells in vivo have been recognized [Blood, 80, 1914 (1992)].

However, though some of splenic stromal cells have been established as a cell line (CF-1 cells), and cytological characteristics thereof have been examined, a specific antibody recognizing surface antigens thereof has been hardly prepared so far, and characteristics thereof have been scarcely known.

Hence, the present inventors have engaged in assiduous studies with a view to developing specific antibodies capable of recognizing splenic stromal cells on the basis of the above information upon splenic stromal cells and the results of the studies, and prepared monoclonal antibodies using the splenic stromal cell lines as antigens for immunization, and as a result, novel monoclonal antibodies unreported so far have been obtained.

And as a result of examining the properties of the obtained monoclonal antibodies, the inventors found that they had the property of causing apoptosis on myeloid cells, and had reported this result previously, and further have found that the antigens recognized by the monoclonal antibodies are identical to IAP (Integrin Associated Protein) and the IAP have functions relating to apoptosis, and that it is possible to differentiate, identify and screen the substances, such as antibodies and the like, that have property of causing apoptosis by using cells which are expressing the IAP, and further have engaged in assiduous studies, which have led to the completion of the present invention.

SUMMARY OF INVENTION

It is the objective of the present invention to provide a method of screening substances having property of causing apoptosis and the like.

This invention relates to a method of screening substances having property of causing apoptosis characterized by using cells which are expressing IAP (Integrin Associated Protein) and screening the substances. The invention relates to the screening method, wherein the cells used are myeloid cells, and relates to pharmaceutical compositions containing as the ingredient the substances obtained by the above screening method. The invention makes it possible to differentiate, identify and screen readily and highly efficiently the substances, such as antibodies and the like, that have property of causing apoptosis on myeloid cells by using cells which are expressing IAP while using specific binding reactions of the substances. The above specific substances thus obtained by the screening method of the invention can be used by virtue of their characteristics as the active ingredient of pharmaceutical compositions such as anticancer agents and medicines for myelocytic leukemia and the like which are useful in the field of remedies for myelocytic leukemia and the like.

DISCLOSURE OF INVENTION

It is the objective and purpose of the present invention to provide a method of screening substances having property of causing apoptosis by using cells which are expressing IAP, and further to provide novel substances having property of causing apoptosis on cells obtained by the above screening method and pharmaceutical compositions as the active ingredient the above substances.

The above monoclonal antibody is remarkably useful as an antibody recognizing antigens causing the apoptosis [it is also called self-destruction of cells, phenomenon that a nuclear chromatin DNA is digested at a nucleosome unit (so-called ladder formation) to result in the death of cells] of myeloid cells and having a function of identifying them or a function of causing apoptosis on myeloid cells. Incidentally, myeloid cells include cells other than lymphoid cells, such as neutrophils, megakaryocytes, myeloblasts, myelocytes, mast cells, macrophages, monocytes and erythroblasts, and the myeloid cells according to the present invention also mean the same as mentioned above. No monoclonal antibody having the property of causing apoptosis on myeloid cells has been known so far other than the above monoclonal antibody, and hence the above monoclonal antibodies are defined to include all monoclonal antibodies having the property of causing apoptosis on myeloid cells.

The monoclonal antibody may be prepared basically as stated below.

Namely, the above monoclonal antibody may be prepared, for example, by using splenic stromal cells derived from an animal administered rG-CSF as antigens, immunizing them according to an ordinary immunization method, cell-fusing the immunized cells according to an ordinary cell fusion method, and cloning the fused cells according to an ordinary cloning method.

As a method of preparing the above monoclonal antibody can be preferably exemplified a method comprising using CF-1 cells, splenic stromal cells of an animal administered rG-CSF established as culture cell line by the present inventors, as the antigen [Blood, Vol. 80, 1914 (1992)], fusing plasma cells (immunocyte) of a mammal immunized with the antigen with myeloma cells of a mammal such as a mouse, cloning the obtained fused cells (hybridomas), selecting clones producing the above antibody recognizing the above cell line among them, and culturing them to recover objective antibody. However, the method is only an example, and in this case, for example, not only the above CF-1 cells but also cell lines derived from human splenic stromal cells obtained according to the case of CF-1 cells may be used as the antigens properly to prepare antibodies binding to objective human myeloid cells in the same manner as in the case of the above CF-1 cells.

In the method of preparing such monoclonal antibodies, mammals to be immunized with the above antigen are not particularly restricted; it is preferable to make selection taking into account suitability with myeloma cells to be used in cell fusion, and preferably a mouse, a rat and a hamster and the like are used.

Immunization is performed according to an ordinary method, for example, by administering splenic stromal cells such as the above CF-1 cells and the like into abdominal cavity of a mammal by injection. More specifically, it is preferable to administer one diluted with or suspended in a proper amount of PBS or isotonic sodium chloride solution to an animal several times every month. It is preferable to use splenic cells removed after the final administration of the above cells as immunocytes.

As a myeloma cell of a mammal as the other parent cell fused with the above immunocytes can be used preferably known various cells including P3(P3x63Ag8.653) [J. Immunol., 123, 1548 (1978)], p3-U1 [Current Topics in Micro-biology and Immunology, 81, 1–7 (1978)], NS-1 [Eur. J. Immunol., 6, 511–519 (1976)], MPC-11 [Cell, 8, 405–415 (1976)], Sp2/0-Ag14 [Nature, 276, 269–270 (1978)], FO [J. Immunol. Meth., 35, 1–21 (1980)], S194 [J. Exp. Med., 148, 313–323 (1978)] and R210 [Nature, 277, 131–133 (1979)].

The cell fusion of the above immunocyte and a myeloma cell may be performed basically according to an ordinary method, for example, a method by Milstein et al. [Methods Enzymol., 73, 3–46 (1981)] and the like.

More specifically, the above cell fusion may be performed, for example, in an ordinary nutrition medium in the presence of a fusion-accelerating agent. As a fusion-accelerating agent, polyethylene glycol (PEG) and Sendai virus (HVJ) and the like, and furthermore, adjuvants such as dimethyl sulfoxide and the like may be added properly if required in order to enhance the fusing effect. Regarding the ratios of immunocytes and myeloma cells, the former is preferably used in an amount 1–10 times that of the latter. Examples of a medium used in the above cell fusion include a RPMI-1640 medium and a MEM medium suitable for the proliferation of the above myeloma cell and other mediums ordinarily used for the culture of this kind of cell, and in addition, supplementary serum such as fetal bovine serum (FBS) may be used together.

Cell fusion is performed by mixing prescribed amounts of the above immunocytes and myeloma cells in the above medium, adding a PEG solution preheated to about 37° C., for example, PEG with an average molecular weight of the order of 1,000–6,000 to the medium, ordinarily, at a concentration of about 30–60% (W/V), and mixing them. Subsequently, by repeating the operations of adding proper mediums one after another, centrifuging the reaction mixture and removing the supernatants can be formed objective hybridomas.

Said hybridomas are selected by culturing in an ordinary selective medium, for example, a HAT medium (medium supplemented with hypoxanthine, aminopterin and thymidine). The culture in the HAT medium is continued for a period sufficient for cells other than objective hybridomas (non-fused cells) to die out, ordinarily for several days to several weeks. Subsequently, the screening and monocloning of the hybridomas producing the objective antibodies are performed according to ordinary limiting dilution analysis.

The prepared hybridomas producing the above monoclonal antibodies may be subcultured in an ordinary medium and stored in liquid nitrogen for a long time.

In order to collect the above monoclonal antibodies from the hybridomas may be employed a method comprising culturing the hybridomas according to an ordinary method, and obtaining them from the supernatants, or a method comprising administering a hybridoma into a appropriate mammal to proliferate, and obtaining them from its ascites. The former is suitable for obtaining antibodies with a high purity and the latter is suitable for the mass production of antibodies.

Furthermore, the antibodies obtained according to the above methods may be purified to a high degree employing an ordinary purification means such as a salting-out technique, gel filtration and affinity chromatography and the like.

As the monoclonal antibody, BMAP-1 is used in Example described later, the monoclonal antibody to be used is not limited to the same, and the monoclonal antibody may be any one so far as it has a specific property to be described specifically in Example later, namely, a property of causing apoptosis on myeloid cells, and those having the property are included in the scope of the present invention, irrespective of the kind of the same. Next, as cells which are expressing IAP, myeloid cells and the like are exemplified, and for example, transfectant Jurkat cell with murine IAP gene (Genbank, Accession number Z 25524) [The Journal of Cell Biology, 123, 485–496 (1993)] transfected by the usual way and the like are used preferably. The IAP gene is not limited to the murine IAP gene, and it is possible to use another IAP gene, such as human IAP gene and the like. Further, cells which are expressing IAP (for example, human leukemia cell and the like) are used in the same way.

Then, the screening method of the present invention is characterized by using cells which are expressing IAP, and a method of screening substances having property of causing apoptosis by using the cells comprises differentiating, identifying and screening by the usual way the substances, such as monoclonal antibody which recognizes the IAP specifically as an antigen, and fragments thereof, while using the same cells which are not expressing IAP as a blank, and further a definite method of the same is not limited to the specified method.

The monoclonal antibody thus obtained by the screening method of the present invention, fragments thereof, substances having property of causing apoptosis which have a binding ability to IAP and the like can be used by virtue of their characteristics as the active ingredient of pharmaceutical compositions, such as anticancer agents, medicines for myelocytic leukemia and the like which are useful in the field of remedies for myelocytic leukemia and the like.

Needless to say, the establishment of a specific system for identifying and recognizing antigens causing apoptosis on myeloid cells according to utilizing the monoclonal antibody, or for using it as medicine for myelocytic leukemia according to utilizing the specific property thereof, and modification and application thereof are put into practice according to an ordinary method obvious to those skilled in the art.

Figure 1:
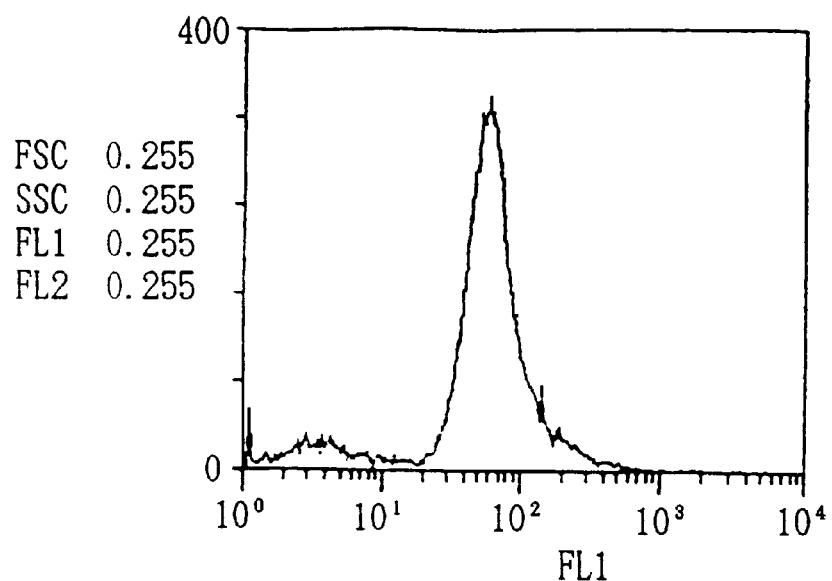
FIG. 1 shows an analysis (a control in the absence of an antibody, CF-1 cell) according to immunofluorescence.

EXPLANATION OF SYMBOLS a: DNA of the thymus of a mouse administered BMAP-1(24hours)

b: DNA of the bone marrow of a mouse administered BMAP-1 (24 hours)

c: DNA of the bone marrow of a mouse administered BMAP-1 (8 hours)

d: DNA of the bone marrow of a mouse administered BMAP-1 (4 hours)

e: DNA of the bone marrow of a non-treated mouse (bone marrow cells)

f: Molecular weight marker

BEST MODE FOR CARRYING OUT THE INVENTION

Next, the present invention will be described further in detail according to Reference Example and Example, but the present invention is not restricted to the Example.

Reference Example
Establishment of Splenic Stromal Cells and Their Characteristics Thereof
1) Establishment of Splenic Stromal Cells A splenic stromal cell line was established from the primary culture of the splenic cells of a C57BL/6J mouse administered rG-CSF 100 μg/kg for 5 days according to serial administration of rG-CSF. Namely, this spleen was removed after the administration of rG-CSF under germ-free conditions, cultured in a 25–cm² plastic flask (Corning Co.) for 6 weeks and in an Isocove's modified Dulbecco's medium (IMDM) (Boehringer-Mannheim Co.) with 10% heat-inactivated fetal bovine serum (FBS) (Sanko Junyaku, Tokyo), 100 U/ml penicillin and 100 μg/ml streptomycin in an incubator under the condition of 37° C. and 5% $CO_2$, and the medium was exchanged for a fresh growth medium twice a week.

In the confluent culture, the adherent cell populations (stromal cells) were harvested from the flask by using 0.05% trypsin plus 0.02% EDTA (Sigma Chemical Co.) in Ca-, Mg-free PBS, and were transferred into new flasks. These passages were repeated approximately once or twice a week. In the early passages (1st through 10th passages), the split ratio of the cells was ¼ to ⅛, and subsequently the ratio was ¹⁄₁₆ to ¹⁄₃₂. The stromal cells became homogeneous and fibroblastoid after approximately the 10th passage. At the 20th passage, these stromal cells were harvested as described above and forwarded to cell cloning by using a limiting dilution technique; cell cloning was repeated twice to establish a stromal cell line (CF-1 cell line).

Subsequently, these cells were maintained in 5 ml of IMDM supplemented with 10% heat-inactivated FBS in a 25–cm² flask (Corning Co.), and subcultured once every 5 days at the split ratio of 1/32. Splenic stromal cell lines can be established from other animals than mouse; for example, human splenic stromal cell lines can be established using the same method as described above by transforming the cells with an SV-40 adenovirus vector [J. Cell. Physiol., 148, 245 (1991)].

2) Characteristics of CF-1 Cells

CF-1 cells established as a cell line as described above were examined for alkaline phosphatase, acid phosphatase, β-glucuronidase, α-naphthyl acetate esterase and oil red O using standard cytochemical techniques. CF-1 cells were also characterized by immunoenzymatic histochemistry using the following monoclonal and polyclonal antibodies: macI (Sero Tec.); factor VIII-related antigen (Dakopatts); and collagen type I, collagen type III and fibronectin (Chemicon International Inc.). Phagocytosis was tested by latex bead uptake (particle diameter: 1.09 μm; Sigma), and the potency of CF-1 cells to convert to adipocytes was tested by exposure to $10^{-6}$ mol/l hydrocortisone phosphate (Sigma) in a 25-cm$^2$ flask for 4 weeks after the confluent culture.

As a result, the CF-1 cells were negative for alkaline phosphatase, factor VIII-related antigen, mac I and phagocytosis, whereas they were positive for collagen type I, collagen type III and fibronectin. CF-1 cells were not converted to adipocytes during 4 weeks in a confluent culture with $10^{-6}$ mol/l hydrocortisone, although CF-1 cells had only traces of lipid. From these data, CF-1 cells do not have the characteristics of preadipocytes, macrophages and endothelial cells, and therefore it has become obvious that they are derived from stromal cells different from them.

3) Maintenance of Hematopoietic Stem Cells by CF-1 Cells

To examine whether hematopoietic stem cells are maintained by CF-1 cells or not, CFU-S assays (assays of spleen colonies-forming cells) were performed by the technique of Till and McCulloch. Ten mice per group were irradiated with 900 cGy (MBR-1520R; Hitachi, Tokyo) and injected intravenously with bone marrow mononuclear cells (BM cells) ($1.0 \times 10^5$/head, $5.0 \times 10^4$/head, or $2.5 \times 10^4$/head) and CF-1 cells ($1.0 \times 10^5$/head), and colonies in the spleen were counted on the 12th day as CFU-S clones (spleen colonies).

As a result, when bone marrow mononuclear cells (BM cells) and CF-1 cells were transplanted into irradiated mice, the number of spleen colonies of every group of BM cells increased significantly (between 1.4–1.8 times) as compared to the mice without CF-1 cells, and, on the 12th day after the transplantation, the survival ratios of the mice transplanted with BM cells and CF-1 cells were higher than those with only BM cells, showing a low death rate; hence it has become apparent that hematopoietic stem cells are maintained by CF-1 cells.

The embodiment of the invention will be described in detail hereinafter.

EXAMPLE

Establishment of Monoclonal Antibodies

1) Antigens and Immunization

Immunization was performed by using CF-1 cells obtained in the above Reference Example as antigens. The cells were cultured in an incubator under the condition of 5% $CO_2$ and 37° C., using an Isocove's modified Dulbecco's medium (IMDM) (Boehringer-Mannheim Co.) supplemented with 10% fetal bovine serum (FBS; Sanko Junyaku) as a medium.

The cells were treated with 1mM EDTA/PBS, and removed from a culture flask according to pipetting. The cells were suspended into 1mM EDTA/PBS at the cell number of about $1 \times 10^7$/ml, and administered to a Wistar Imamich rat (7-week-old, female; Animal Breeding Research Laboratory). One ml of cells of about $1 \times 10^7$/ml were injected into the abdominal cavity of the rat at the initial immunization, and 1 ml of cells of about $1 \times 10^7$/ml were administered additionally one month later. Further, 1 ml of cells of about $1 \times 10^7$/ml were administered additionally several times at an interval of a month, and after the reactivity between the immunized rat antibody and CF-1 cells was recognized, 1 ml of cells of $1 \times 10^8$/ml were administered as the final immunization. Three days after the final immunization, the rat was killed to remove spleen.

2) Cell Fusion

After the spleen removed from the rat was minced, splenic cells isolated were centrifuged, suspended in an IMDM medium (Boehringer-Mannheim Co.), and washed intensively. On the other hand, the cells obtained by cultured mouse myeloma cell line Sp2/0-Ag14 [Nature, 276, 269–270 (1978)] in an IMDM (Boehringer-Mannheim Co.) supplemented with 10% fetal bovine serum (FBS; Sanko Junyaku) were washed in the above IMDM medium in the same manner, and $1 \times 10^8$ thereof and $2 \times 10^8$ of the above splenic cells were put into a centrifuge tube and mixed to perform cell fusion by polyethylene glycol 4000 (Nakarai Kagaku) according to an ordinary procedure [Clin. Exp. Immunol., 42, 458–462 (1980)].

Subsequently, the obtained fused cells were dispensed into a 96-well plate with an IMDM medium supplemented with 20% FBS, and cultured in an incubator under the condition of 37° C. and 5% $CO_2$. They were replaced into a HAT selective medium gradually from the following day, and continued to be cultured.

After the start of the culture, the supernatants were replaced into a new HAT medium twice a week to continue the culture and maintain the proliferation.

Next, the obtained fused cells were cloned according to an ordinary procedure using limiting dilution analysis. Namely, only clones having strong binding properties to antigens were cloned according to an ordinary procedure employing limiting dilution analysis by examining binding properties thereof to the antigens, utilizing antibodies in the supernatants of the above fused cells.

3) Screening

The screening of fused cells (hybridomas) was performed according to indirect fluorescent antibody technique using flow cytometry.

The screening of clones producing objective antibodies was performed using CF-1 cells as target cells. Namely, cells suspended in a reaction buffer (PBS supplemented with 2% FBS and 0.02% $NaN_3$) were centrifuged and recovered as pellets, then suspended in 100 μl of the hybridoma culture supernatants (about $1 \times 10^6$/100 μl) and reacted at 4° C. for 1 hour. After they were washed with the above buffer once, an FITC-labelled goat anti-rat IgG (FC) antibody (Chemicon) was added thereto and incubated for 1 hour. After they were washed once, they were analyzed according to flow cytometry (FACScan, Becton Dickinson).

4) Purification of Antibodies

The fused cells screened in the manner of the above 3) were cultured according to an ordinary procedure, and antibodies produced in the supernatants were separated according to an ordinary procedure, and purified.

Namely, hybridomas were recovered from wells with high antibody titers to the antigens, spread in a tissue culture plastic dish (Corning Co.), cultured under the condition of 5% $CO_2$ and 37° C. proliferated, and purified according to an ordinary procedure to obtain monoclonal antibodies GSPST-1 and BMAP-1.

Regarding GSPST-1, obtained cells were injected into the abdominal cavity of a BALB/cAJc1-nu nude mouse (8-week-old, male, Nippon Kurea). Produced ascites was recovered after 10–14 days, salted out with 33% ammonium sulfate, and dialyzed with PBS. Regarding the BMAP-1 antibody, it was cultured in a large scale in an Iscove's modified MEM medium supplemented with 10% FBS, and the supernatants were concentrated, salted out with 33% ammonium sulfate, dialyzed with PBS, purified again by means of a protein A column kit (Amersham), and dialyzed with PBS. Incidentally, in the above Example was described the case in which the CF-1 cells were used as antigens for immunization; however, it is possible to establish a monoclonal antibody in the same manner also in case of using other stromal cells having potency supportive of hematopoietic stem cells.

A hybridoma producing the above monoclonal antibody BMAP-1 is a novel fused cell prepared from a Wistar Imamich rat splenic cell and a mouse myeloma cell line SP2/0-Ag14 as parent cells, and was deposited on 9 August, 1993, under the name of BMAP-1 (rat mouse hybridoma) with the accession number of FERM BP-4382, at National Institute of Bioscience and Human Technology, Agency of Industrial Science and Technology in Japan [address: 1–3, Higashi 1-chome, Tsukuba-shi, Ibaraki 305, Japan], international depositary authority according to Budapest Treaty on the international recognition of the deposit of microorganisms for the purpose of patent procedures.

5) Properties of Antibodies
(i) Reactivity of Antibodies
(Reactivity to CF-1 Cells)

Figure 2:
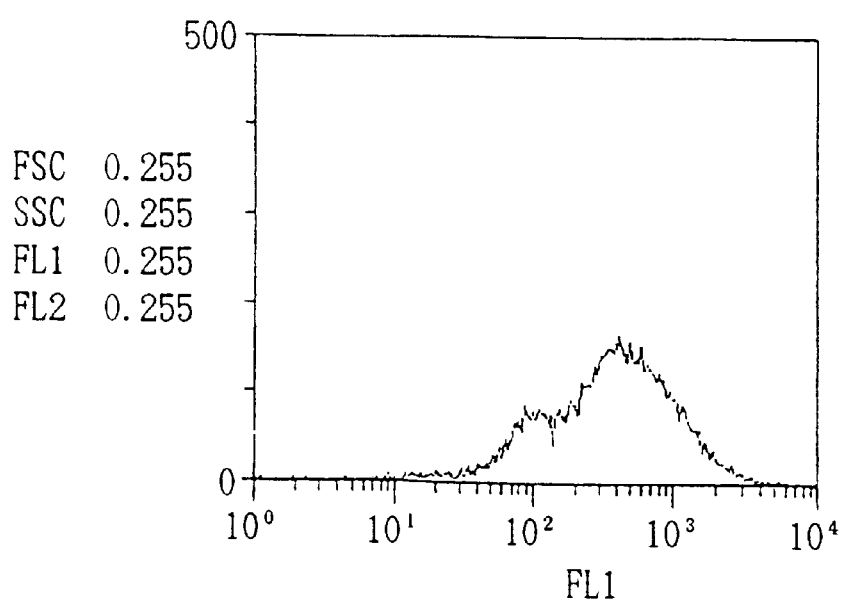
FIG. 2 shows an analysis of the binding properties of the GSPST-1 antibody to CF-1 cells according to immunofluorescence.
Figure 3:
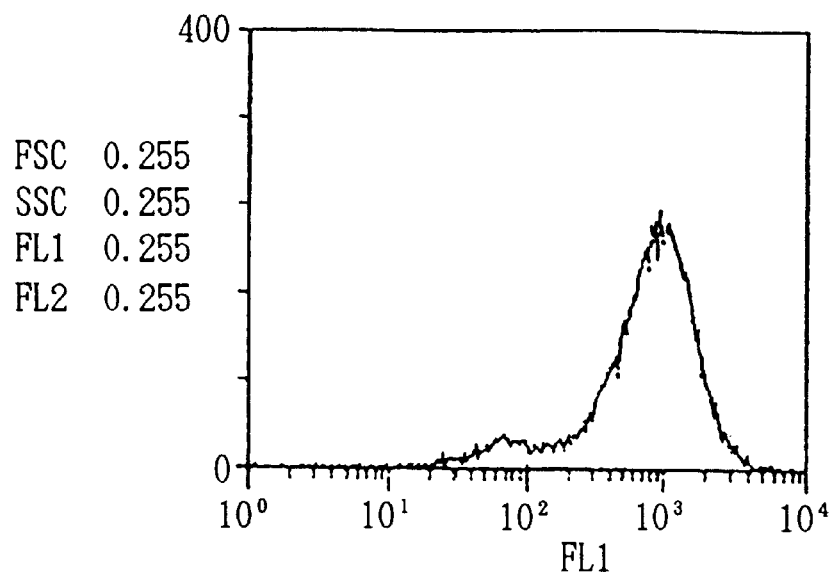
FIG. 3 shows an analysis of the binding properties of the BMAP-1 antibody to CF-1 cells according to immunofluorescence.

The results of examining the reactivity of the obtained monoclonal antibodies GSPST-1 and BMAP-1 to CF-1 cells according to immunofluorescence analysis are shown in FIG. 1 through FIG. 3. Here, FIG. 1 shows the results of analysis of the control in the absence of an antibody, FIG. 2 the results of analysis of the binding properties of GSPST-1 to CF-1 cells, and FIG. 3 the results of analysis of the binding properties of BMAP-1 to CF-1 cells. In the drawings, vertical axes show relative number of cells and transverse axes fluorescence intensity.

As is apparent from FIG. 1 through FIG. 3, it has been revealed that monoclonal antibodies GSPST-1 and BMAP-1 have properties binding to CF-1 cells and recognize surface antigens of CF-1 cells.

(Reactivity to Bone Marrow Cells)

Figure 4:
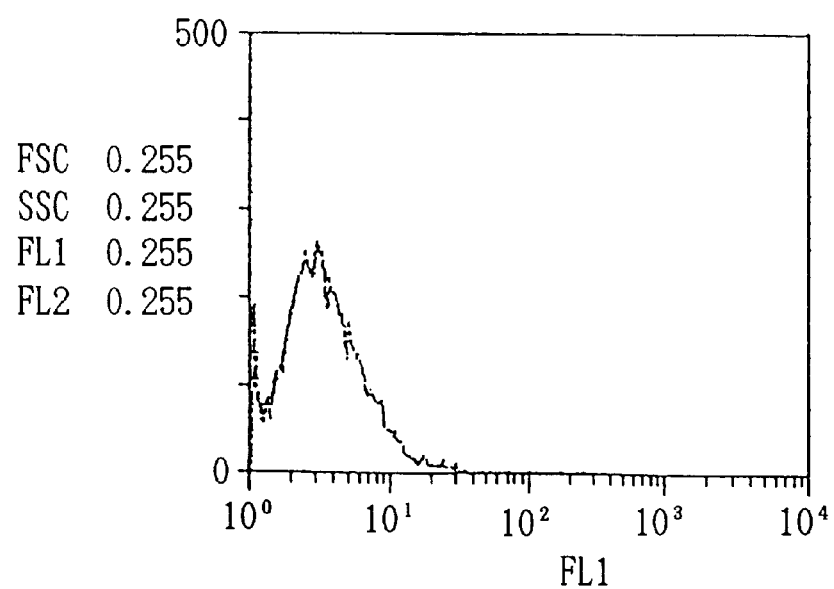
FIG. 4 shows an analysis (a control in the absence of an antibody, bone marrow cell) according to immunofluorescence.
Figure 5:
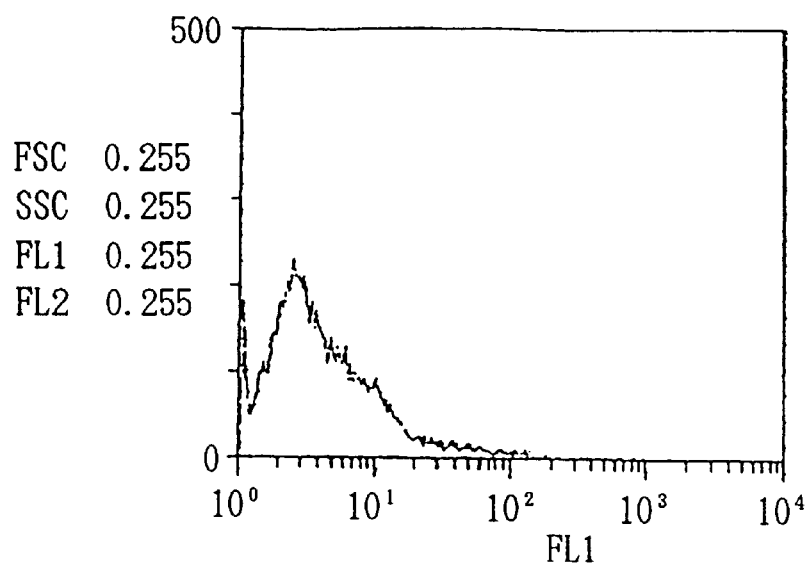
FIG. 5 shows an analysis of the binding properties of the GSPST-1 antibody to bone marrow cells according to immunofluorescence.
Figure 6:
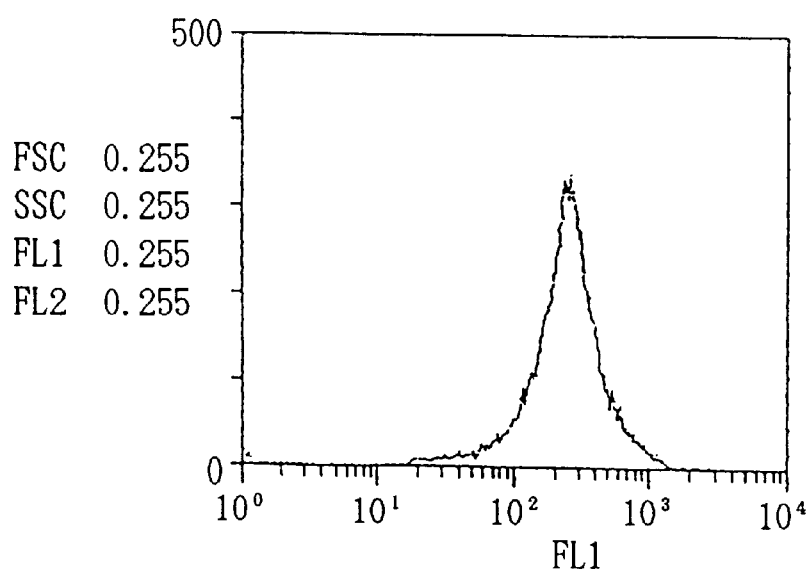
FIG. 6 shows an analysis of the binding properties of the BMAP-1 antibody to bone marrow cells according to immunofluorescence.

Next, the results of analysis of the reactivity of GSPST-1 and BMAP-1 to normal bone marrow cells according to flow cytometry (FACScan, Becton Dickinson) are shown in FIG. 4 through FIG. 6. Here, FIG. 4 shows the results of analysis of the control in the absence of an antibody, FIG. 5 the results of analysis of the binding properties of GSPST-1 to bone marrow cells, and FIG. 6 the results of analysis of the binding properties of BMAP-1 to bone marrow cells. In the drawings, vertical axes show relative number of cells and transverse axes fluorescence intensity.

As is shown in FIG. 4 through FIG. 6, it has been revealed that GSPST-1 has not a property binding to bone marrow cells at all, and that BMAP-1 has a property binding to all bone marrow cells. (Reactivity to Myelocytic Leukemic Cell Line (NFS-60))

Figure 7:
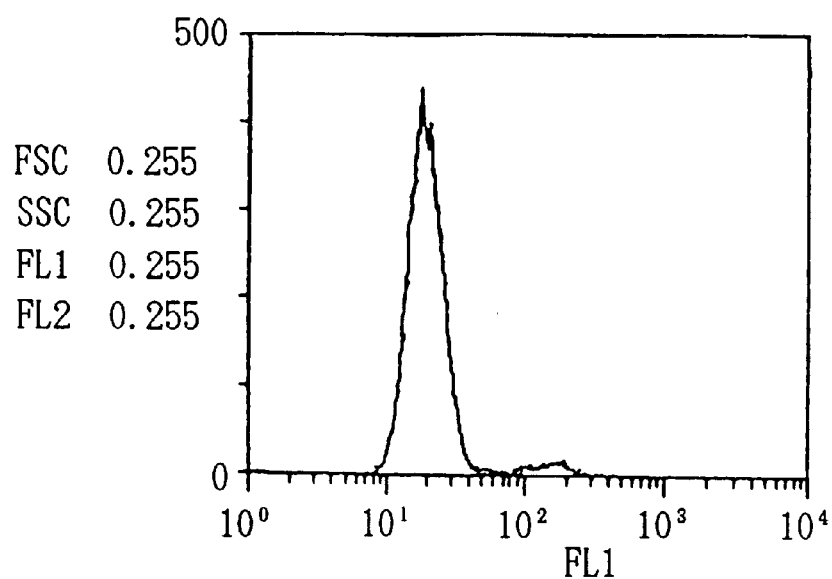
FIG. 7 shows an analysis (a control in the absence of an antibody, NFS-60) according to immunofluorescence.
Figure 8:
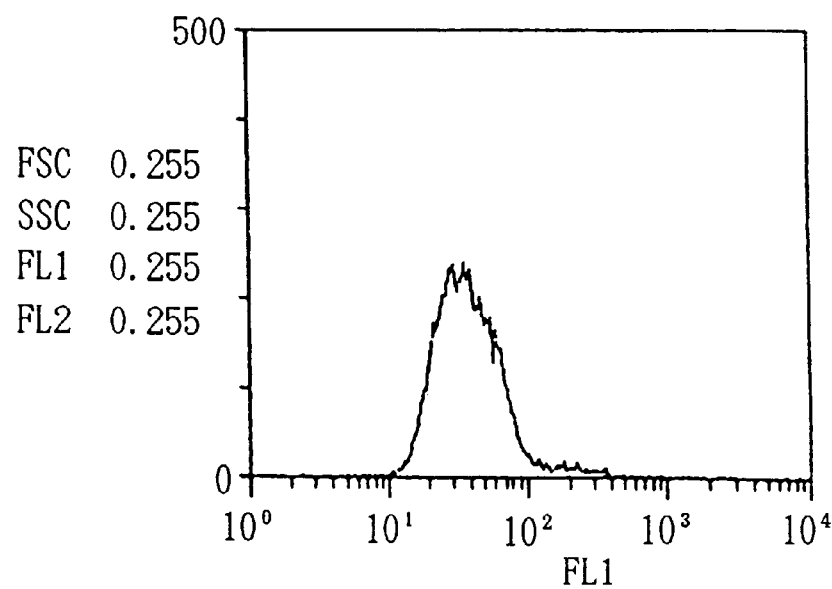
FIG. 8 shows the binding properties of the GSPST-1 antibody to NFS-60 cells according to immunofluorescence.
Figure 9:
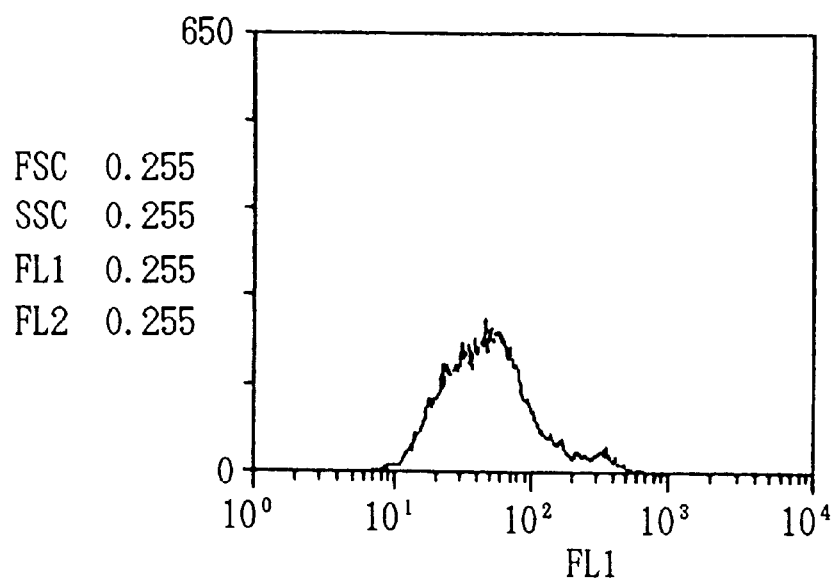
FIG. 9 shows an analysis (a control according to rat IgG1, NFS-60) according to immunofluorescence.
Figure 10:
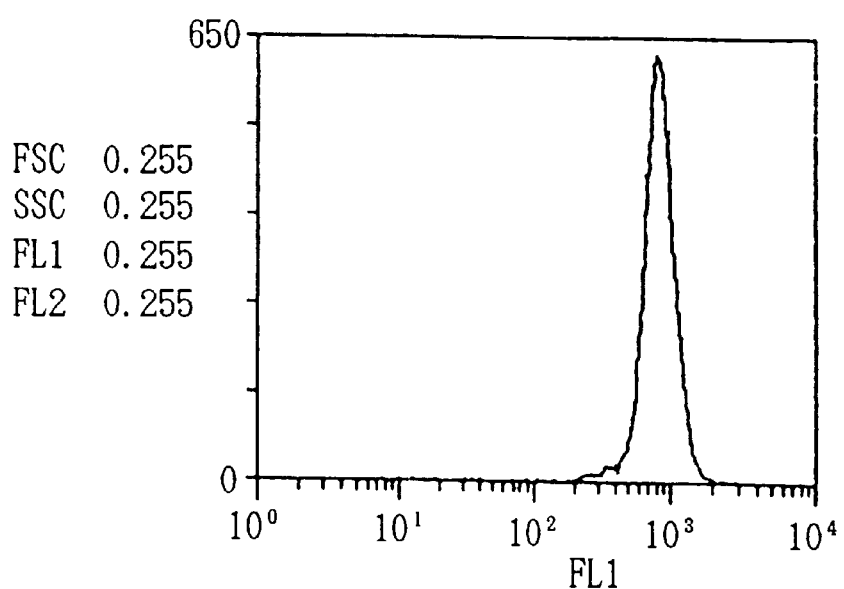
FIG. 10 shows the binding properties of the BMAP-1 antibody to NFS-60 cells according to immunofluorescence.

The results of analysis of the the reactivity of GSPST-1 and BMAP-1 to NFS-60 cells [Proc. Natl. Acad. Sci. USA, 82, 6687–6691 (1985)] according to flow cytometry (FACScan, Becton Dickinson) are shown in FIG. 7 through FIG. 10. Here, FIG. 7 shows the results of analysis of the control in the absence of an antibody, FIG. 8 shows the results of analysis of the binding properties of GSPST-1 to NFS-60 cells, FIG. 9 shows the results of analysis of the control using rat IgG1 on the market (Zymed) and FIG. 10 shows the results of analysis of the binding properties of BMAP-1 to NFS-60 cells. In the drawings, vertical axes show relative numbers of cells and transverse axes fluorescence intensity.

As is shown in FIG. 7 through FIG. 10, it has been revealed that GSPST-1 does not react with NFS-60 cells, and that BMAP-1 has a property binding to NFS-60 cells.
(Assay for BMAP-1 to Inhibit Proliferation of NFS-60 Cells)

Figure 11:
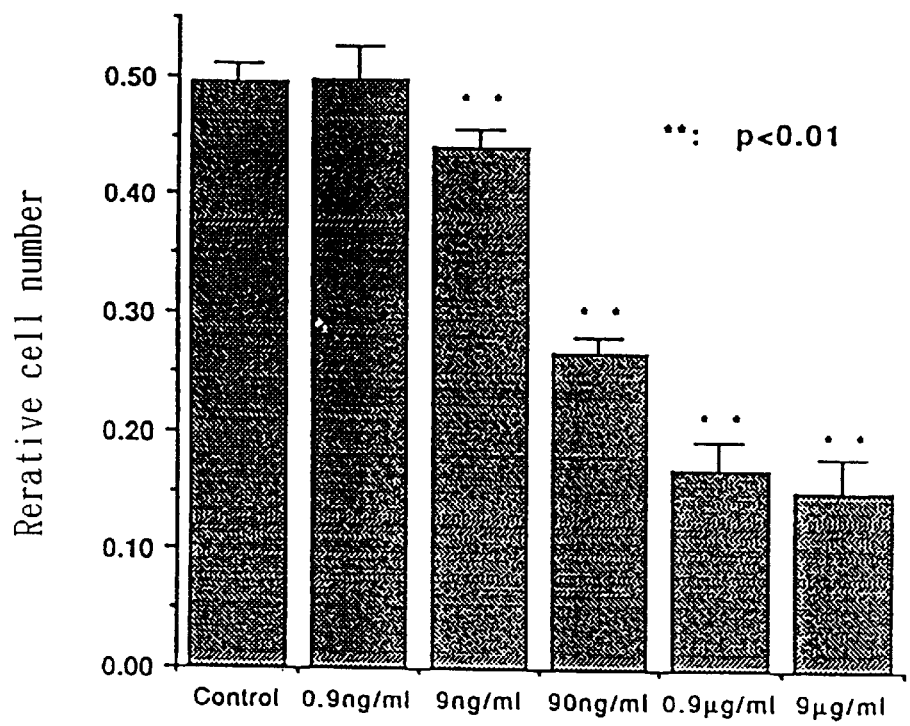
FIG. 11 shows an assay for the monoclonal antibody (BMAP-1) to inhibit NFS-60 cell proliferation.
Figure 12:
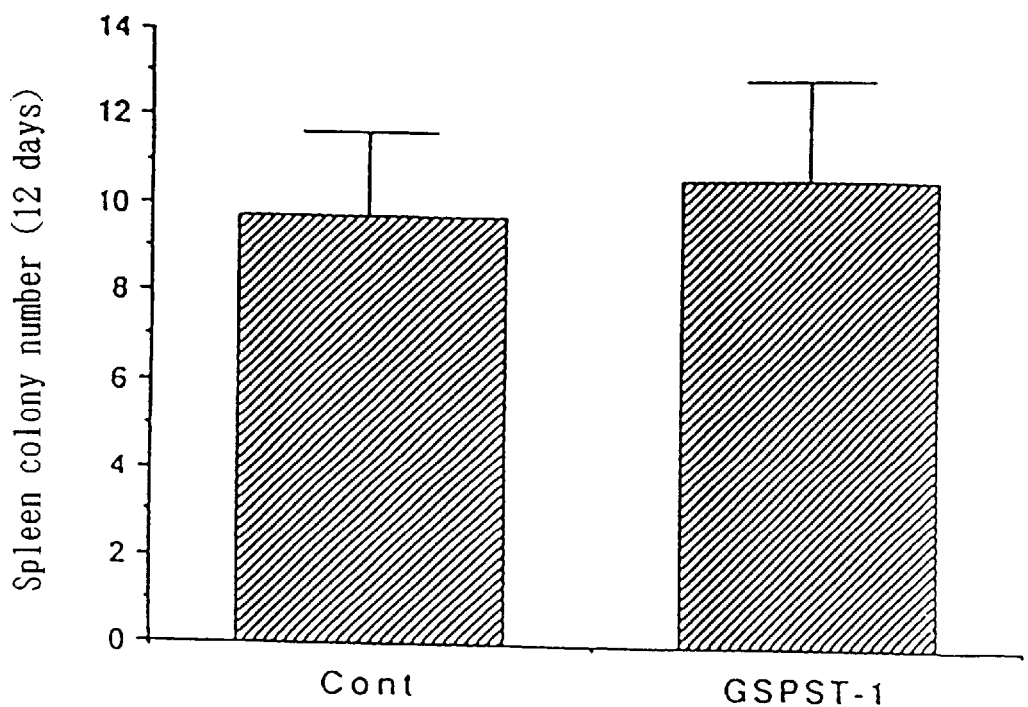
FIG. 12 shows an assay for the monoclonal antibody (GSPST-1) to inhibit the bone marrow transplantation.
Figure 13:
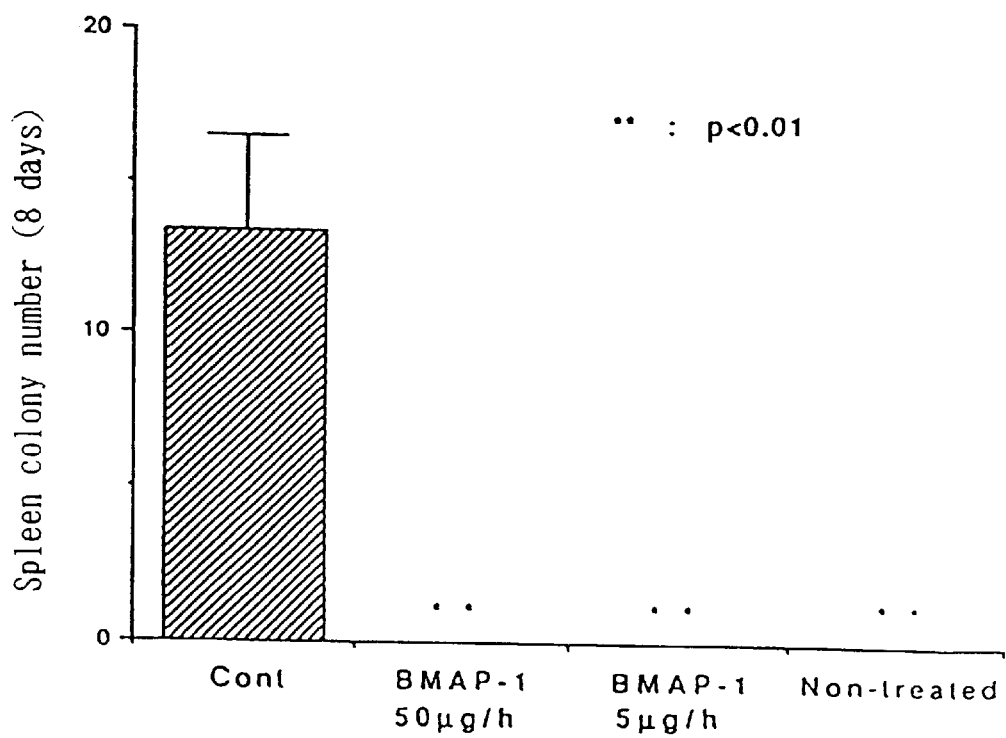
FIG. 13 shows an assay for the monoclonal antibody (BMAP-1) to inhibit the bone marrow transplantation.

The results of examining the action of BMAP-1 to NFS-60 cells in the presence of G-CSF 100 ng/ml and cycloheximide $10^{-9}$ M according to the MTT assay method are shown in FIG. 11. Using culture plates with 96 wells, 10 $\mu$l/well of BMAP-1 solution were added at concentrations of 0, 1, 10, 100 ng/ml, and 1, 10 $\mu$g/ml to $4\times10^3$/well/100 $\mu$l of NFS-60 cells, and two days after the numbers of living cells were measured according to the MTT method. It has been revealed as shown in FIG. 11 that the proliferation of NFS-60 cells 1is inhibited remarkably by BMAP-1.
(ii) Typing of Antibodies Next, as a result of typing the subclass of IgG of the obtained monoclonal antibodies [using a rat Mono Ab-ID-Sp kit (Zymed) and a biotin-labelled mouse anti-rat IgG1 antibody (Zymed)], it has become apparent that GSPST-1 is IgG2a, and that BMAP-1 is IgG1.
(iii) Potency Inhibiting Bone Marrow Transplantation Next, a test upon the inhibition of bone marrow transplantation was performed using these antibodies to examine characteristics thereof. The results are shown in FIG. 12 and FIG. 13. As is shown in FIG. 12 and FIG. 13, while BMAP-1 has the effect inhibiting the bone marrow transplantation, the effect has not been found in GSPST-1. Namely, the above results were obtained by administering $1.0\times10^5$/head of bone marrow cells and monoclonal antibodies to C57BL/6J mice, irradiated at a fatal dose of radiation (900 cGy), through the veins of tails, and counting the number of spleen colonies. Incidentally, "Non-treated" in FIG. 13 shows the case with no administration of bone marrow cells.

Figure 14:
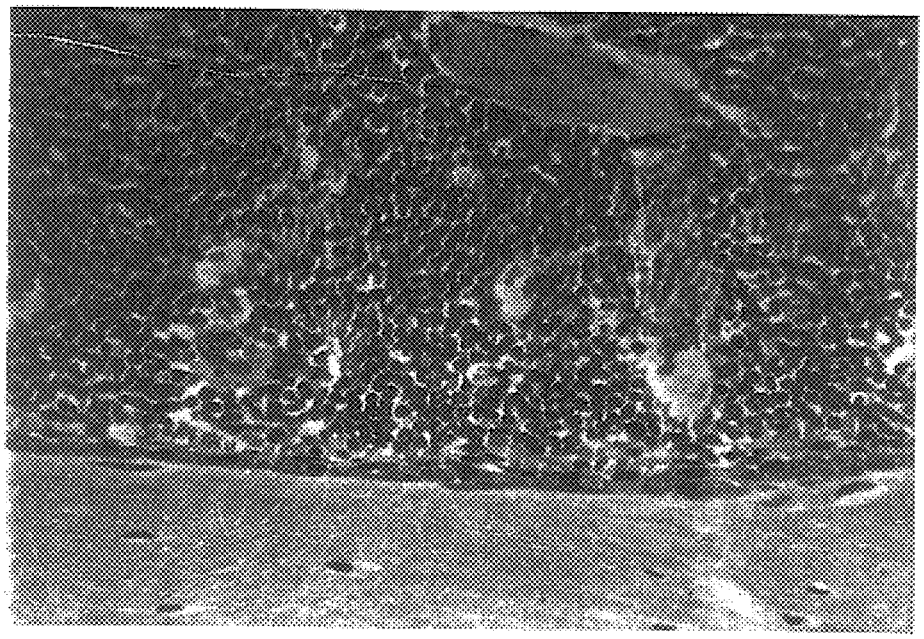
FIG. 14 is an explanatory view [microphotograph (stained with H. E.) of bone marrow samples (×400)] showing dead bone marrow cells (2) on 6 days after the administration of the monoclonal antibody BMAP-1 of the present invention, and the control (1) in the absence of the antibody.
Figure 14:
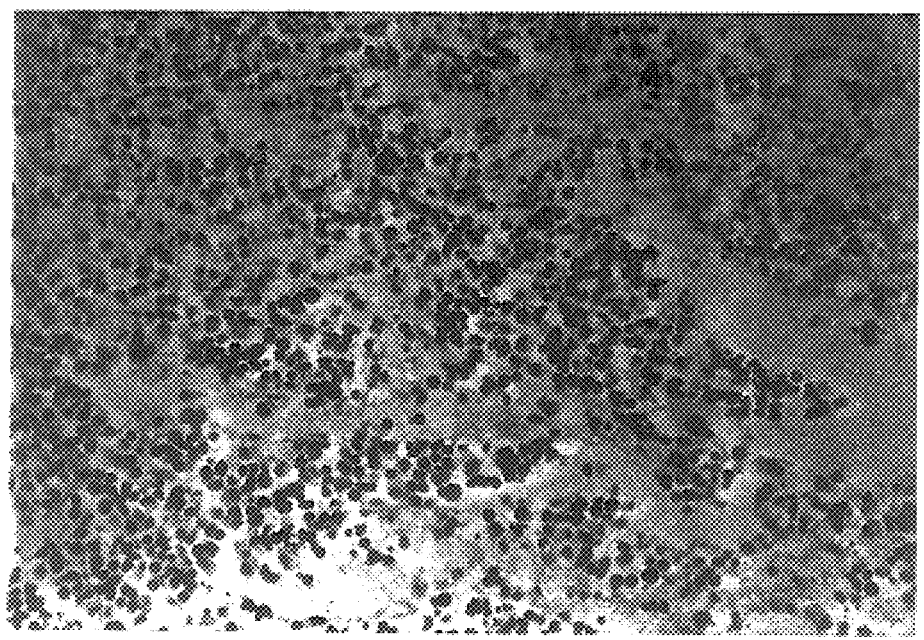
Figure 15:
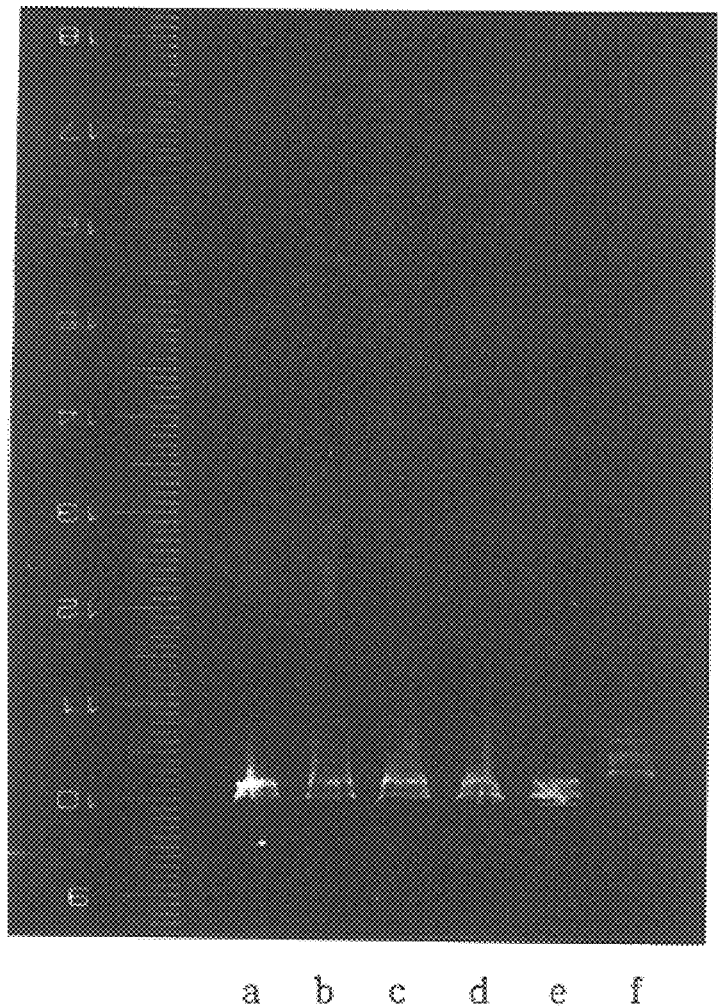
FIG. 15 is an explanatory view (migration-photo according to electrophoretic chromatography) showing the ladder formation of the DNA of bone marrow cells observed when the monoclonal antibody BMAP-1 of the present invention was administered.

As is shown in FIG. 13, it has been confirmed that it is because BMAP-1 reacts with bone marrow cells to cause apoptosis that the monoclonal antibody inhibits transplantation completely in the test upon the inhibition of bone marrow transplantation. Namely, when a hybridoma producing BMAP-1 was administered into the abdominal cavity of a nude mouse, it died at the time when its ascites was stored in a small amount. In addition it has been revealed that all bone marrow cells died out according to the intravenous administration of 50 $\mu$g/head BMAP-1 to a normal C57BL/6J mouse, and in FIG. 14 is shown a microphotograph backing up the fact that bone marrow cells on 6 days after the intravenous administration of BMAP-1 died out. As is apparent from the microphotograph, it has been observed that not only lymphoid cells but also neutrophils, megakaryocytes, myeloblasts, myelocytes, mast cells, macrophages, monocytes and erythroblasts (so-called myeloid cells) died out. In addition, as a result of investigating the DNAs of the bone marrow cells of a mouse administered 30 $\mu$g/head BMAP-1, apparently ladder formation has been observed as is shown in FIG. 15, and it has been revealed that the above reaction of BMAP-1 to bone marrow cells is due to apoptosis.

The Fc region of the IgG of the BMAP-1 antibody was digested with pepsin (Sigma) and purified by means of a GPC column as F(ab)2, and 33.5 $\mu$g/head (corresponding to 50 $\mu$g/head of the whole IgG) were administered to a C57BL/6J mouse intravenously; as a result of it, it was observed that bone marrow cells died out in the bone marrow. It has become apparent according to the above fact that neither antibody-dependent cell cytotoxicity nor complement-dependent cell cytotoxicity participates in the cell death of bone marrow cells by BMAP-1.

As an antigen causing apoptosis has been reported the Fas antigen of cell surface protein; regarding the Fas antigen, the expressions of mRNAs of it are recognized in the thymus, heart, liver, lungs and ovary, but its mRNAs are scarcely detected in the bone marrow [J. Immunol., 148, 1274–1279 (1992)], and hence it is apparent that antigens recognized by BMAP-1 are different from the conventionally known Fas antigen.

Figure 16:
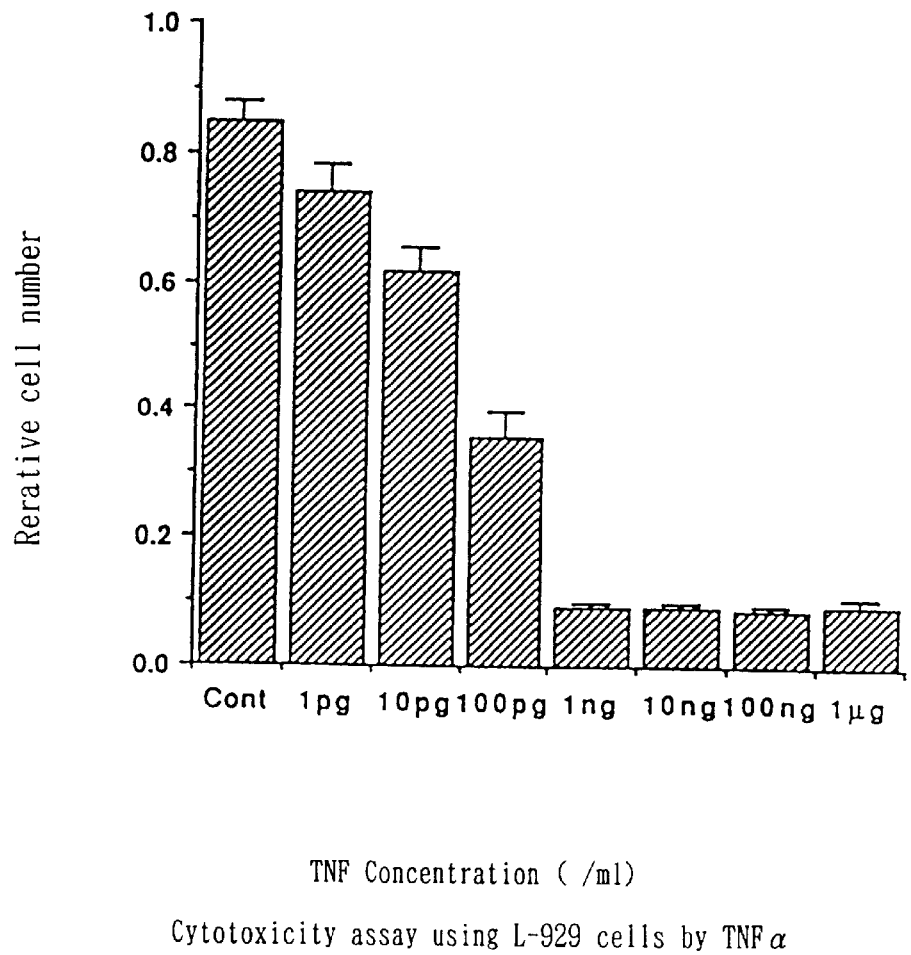
FIG. 16 shows a cytotoxicity assay by TNF
Figure 17:
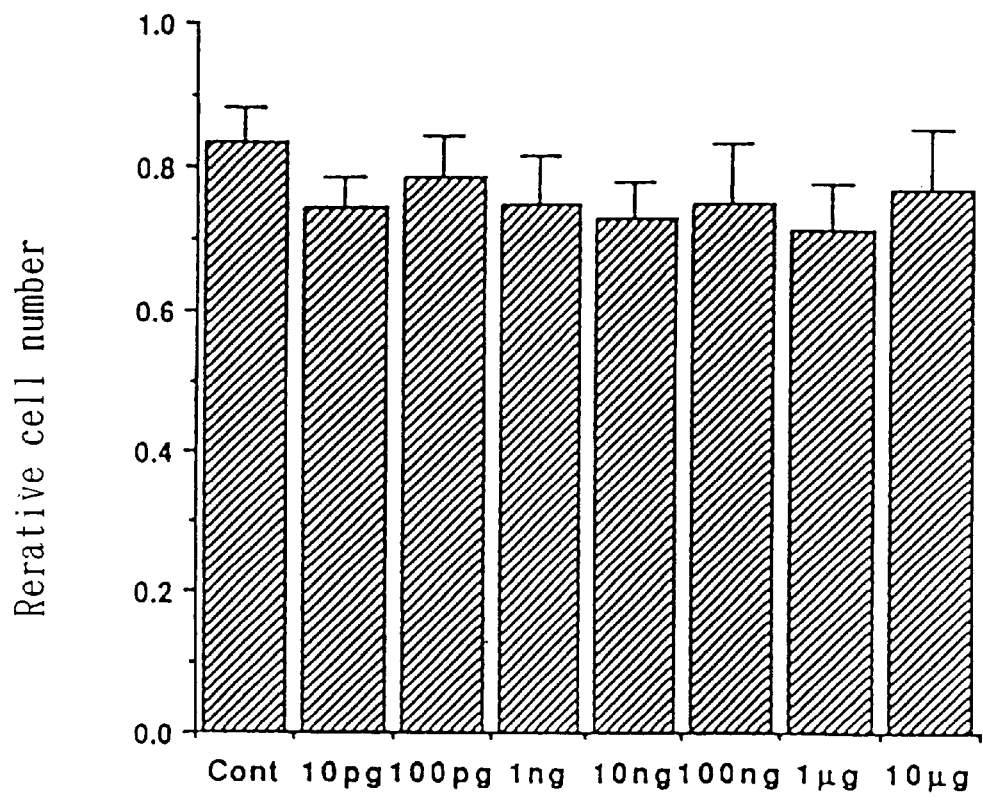
FIG. 17 shows a cytotoxicity assay by the monoclonal antibody (BMAP-1).

Furthermore, in order to make it clear whether an antigen recognized by BMAP-1 would be a TNF receptor or not, the function of BMAP-1 was investigated using L-929 cells reacting with TNF to cause cell death. The final concentrations of a mouse TNF α (Genzyme) were 0, 1, 10, 100 pg/ml, 1, 10, 100 ng/ml, and 1 μg/ml, and those of BMAP-1 were 0, 10, 100 pg/ml, 1, 10, 100 ng/ml, and 1, 10 μg/ml, and the numbers of living cells of L-929 cells were measured according to the MTT method on the second day after the addition of the TNF α and BMAP-1. As a result of it, as shown in FIG. 16, FIG. 17, while L-929 cells were reduced by TNF α remarkably, BMAP-1 had no effect upon L-929 cells. Hence, it has become apparent that an antigen recognized by BMAP-1 is not a TNF receptor.

Figure 18:
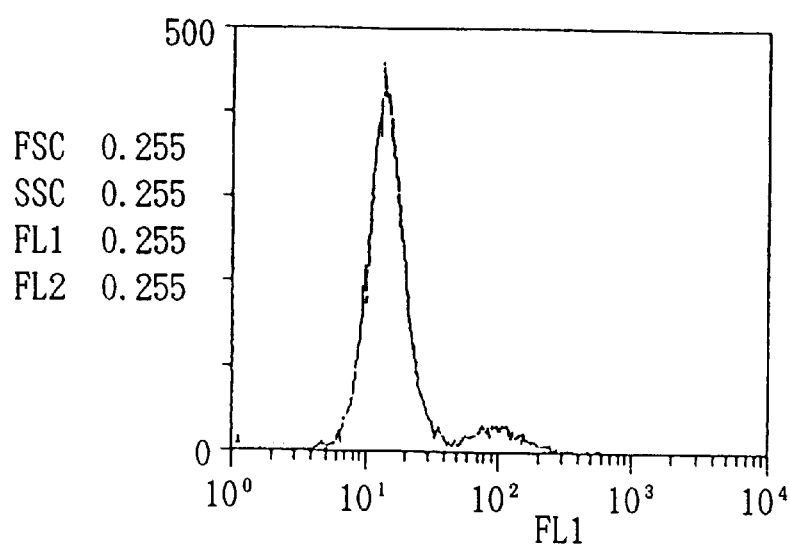
FIG. 18 shows an analysis (a control according to rat IgG2a, BWV1) according to immunofluorescence.
Figure 19:
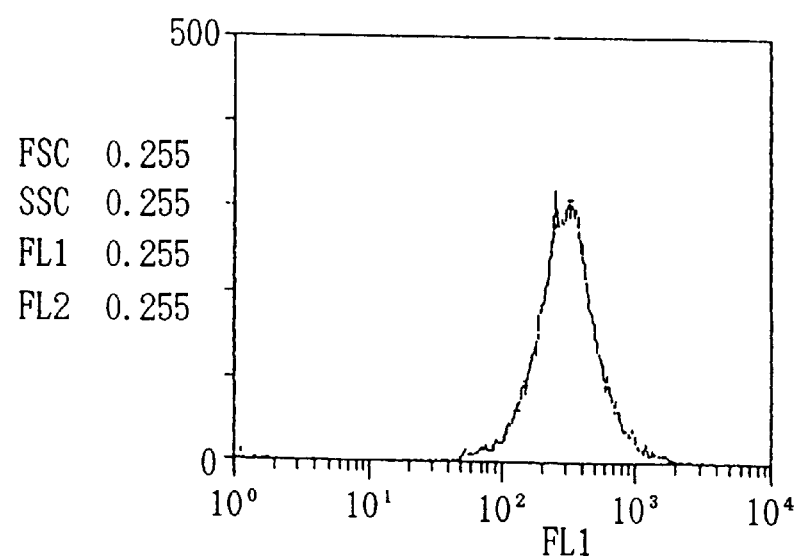
FIG. 19 shows the binding properties of the anti-mouse MHC class I antibody to BWV1 cells according to immunofluorescence.
Figure 20:
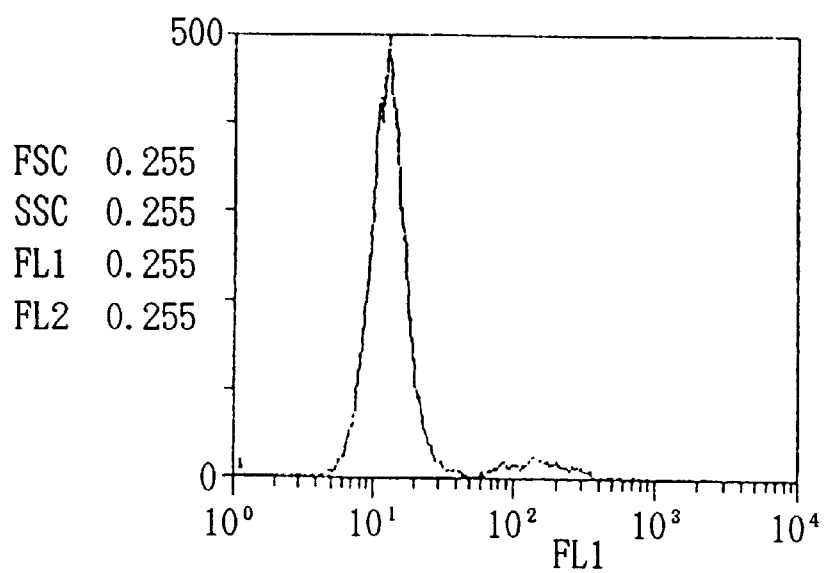
FIG. 20 shows an analysis (a control according to rat IgG1, BWV1) according to immunofluorescence.
Figure 21:
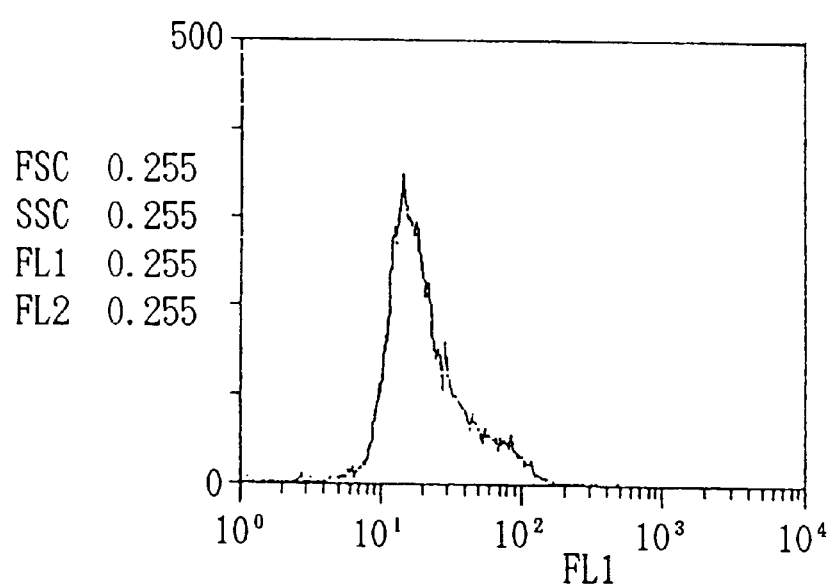
FIG. 21 shows the binding properties of the BMAP-1 antibody to BWV1 cells according to immunofluorescence.

The results of investigating whether antigens recognized by BMAP-1 would be MHC class I antigens or not according to flow cytometry (FACScan, Becton Dickinson) are shown in FIG. 18 through FIG. 21. Here, FIG. 18 shows the results of analysis of the control using rat IgG1 (Zymed), FIG. 19 shows the results of analysis of the binding properties of the anti-mouse MHC class I antibody (rat IgG2a, BMA) to BWV1 cells (mouse lymphoma derived from BW5147 cells), FIG. 20 shows the results of analysis of the control using rat IgG1 (Zymed) and FIG. 21 shows the results of analysis of the binding properties of BMAP-1 to BWV1 cells. In the drawings, vertical axes show relative numbers of cells and transverse axes fluorescence intensity. As a result, BMAP-1 did not recognize BWV1 cells but the MHC class I antibody reacted with BWV1 cells.

As described above, it has been confirmed experimentally that BMAP-1 has the function of causing apoptosis on myeloid cells; according to the present inventor's knowledge, no monoclonal antibody having the property of causing apoptosis on myeloid cells has been reported so far as described above, and hence monoclonal antibodies having such a function are ones found by the present inventors.

It became clear by direct expression cloning that the antigen recognized by BMAP-1 is murine IAP. The action of BMAP-1 was examined employing recombinant cells transfected with murine IAP genes. That is, the action of BMAP-1 on IAP expressing cells was examined by the MTS method and the analysis of DNA fragmentation by a flow cytometry employing recombinant Jurkat cells expressing murine IAP obtainable by inducing IAP genes into Jurkat cells expressing no murine IAP by an ordinary procedure. The results are shown in FIGS. 22 to 26.

Figure 22:
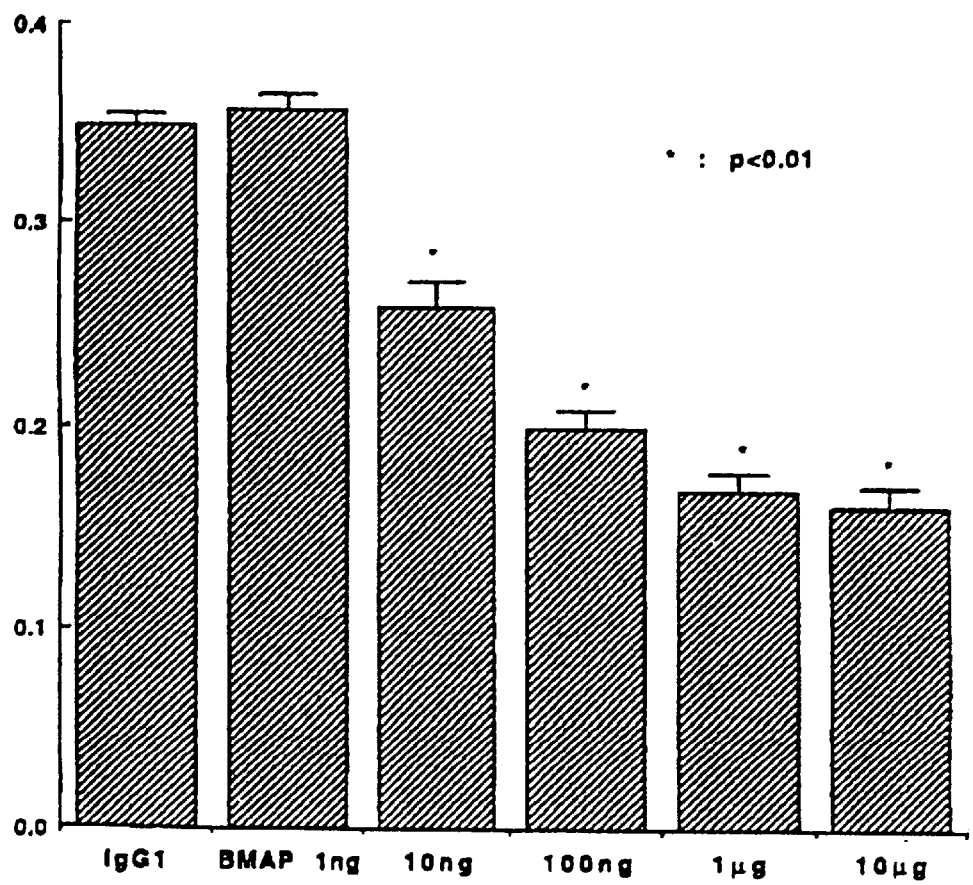
FIG. 22 shows proliferation inhibitory action to BMAP-1 cells (Jurkat cells transfected with murine IAP gene)
Figure 23:
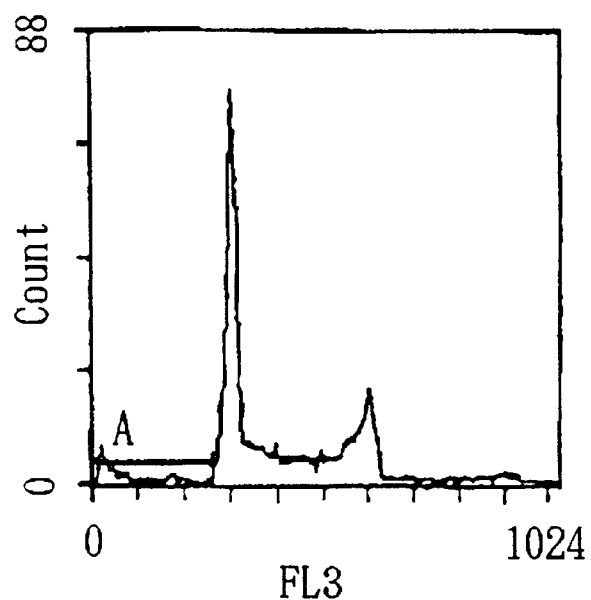
FIG. 23 shows an analysis of apoptosis—an action to Jurkat cells transfected with expression vector (IgG 1 1 μg/ml, A: Apoptosis ratio, 6.2%)

The MTS method is an assay method (Promega) measuring the number of living cells, and the action of BMAP-1 on recombinant Jurkat cells was examined by this method. That is, the number of living cells was measured by the MTS method, employing a culture plate with 96 wells, by adding 1, 10, 100 ng/ml and 1, 10 μg/ml of BMAP-1 at the final concentration and 10 μg/ml of IgG1 as a control to $1 \times 10^4$/well/100 μl of recombinant Jurkat cells in the presence of G418 (final concentration: 1 mg/ml) (produced by Gibco BRL) and culturing them for two days. It became clear as a result of it that, as shown in FIG. 22, the recombinant Jurkat cells are prohibited from proliferating remarkably by BMAP-1.

The analysis of the DNA fragmentation of the recombinant Jurkat cells by BMAP-1 was performed by a flow cytometry (EPICS (registered trademark) XL-MCL, produced by Coulter). That is, employing a culture plate with 6 wells, IgG1 and BMAP-1 were added at the final concentration of 1 μg/ml to $1.5 \times 10^5$/well/3 ml of recombinant Jurkat cells in the presence of G418 (final concentration: 1 mg/ml) (produced by Gibco BRL), and the mixture was cultured for two days and then subjected to measurement. The cells were recovered from the culture plate, and cell pellets were centrifuged at 200×g and fixed in 2 ml of cold 70% ethanol at 4° C. for 60 minutes. Subsequently, the cells were centrifuged and resuspended in 1 ml of PBS. To 0.5 ml of the cell sample were added 0.5 ml of RNAse (Type I-A, Sigma, St. Louis, Mo., USA, 1 mg/ml in PBS) and then the mixture was mixed into 1 ml of a propidium iodide (PI, Sigma, 100 μg/ml in PBS) solution. The mixed cells were incubated at room temperature in a dark place for 15 minutes, then kept at 4° C. in a dark place and subjected to measurement by a flow cytometry.

Figure 26:
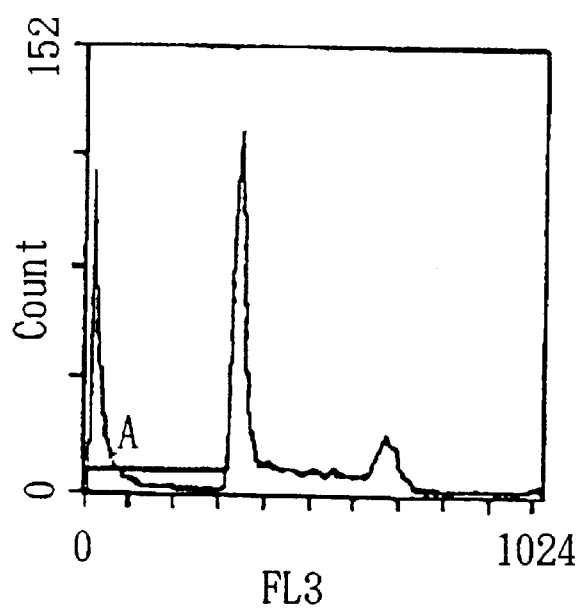
FIG. 26 shows an analysis of apoptosis—an action of BMAP-1 to Jurkat cells transfected with murine IAP gene (BMAP-1 1 μg/ml, A: Apoptosis ratio, 25.6%)

It became clear as a result of it that, as shown in FIG. 26, in the cells transfected with murine IAP genes, apoptosis is caused by BMAP-1.

Figure 24:
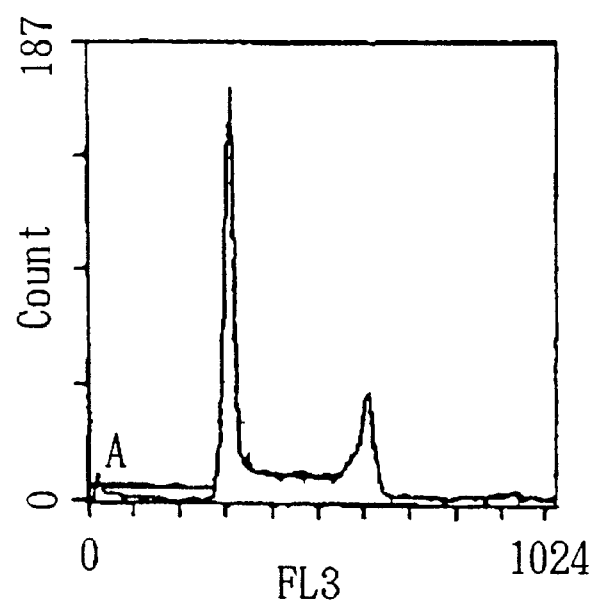
FIG. 24 shows an analysis of apoptosis—an action of BMAP-1 to Jurkat cells transfected with expression vector (BMAP-1 1 μg/ml, A: Apoptosis ratio, 3.5%)
Figure 25:
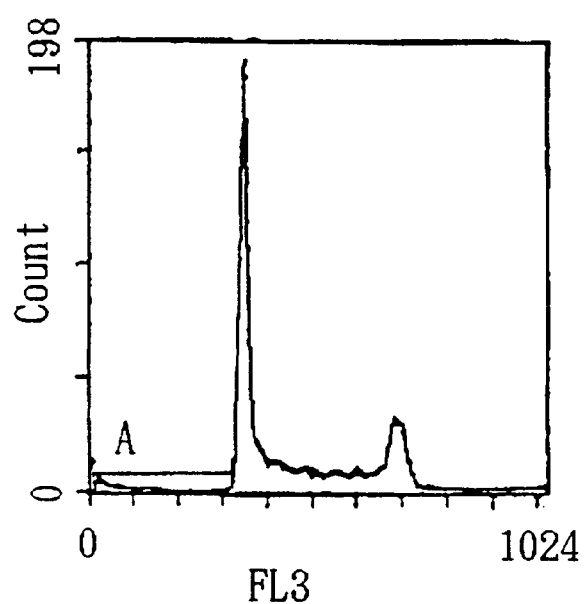
FIG. 25 shows an analysis of apoptosis—an action to Jurkat cells transfected with murine IAP gene (IgG 1 1 μg/ml, A: Apoptosis ratio, 3.2%)

On the other hand, the above action of BMAP-1 was not observed in Jurkat cells with only an expression vector and expressing no murine IAP (FIG. 24). It became clear from these matters that the antigen recognized by the BMAP-1 antibody is identical with IAP, and that IAP has a function related to apoptosis.

According to information at present, as functions of IAP are reported an action of being bound to a β chain of $\alpha_v \beta_3$ of integrin and supporting the bond between $\alpha_v \beta_3$ and vitronectin as a ligand thereof (J. Cell Biol., 123, 485–496 (1993)), an action of causing the flow of $Ca^{2+}$ to the endothelium in adhesion between neutrophils and the endothelium (J. Biol. Chem., 268, 19931–19934 (1993)) and an action of supporting neutrophils to pass through the endothelium (Proc. Natl. Acad. Sci. USA, 92, 3978–3982 (1995)); however, no function related to apoptosis has been reported.

Since BMAP-1 is one of monoclonal antibodies being bound to myeloid cells and causing apoptosis in myeloid cells, as described above, it becomes possible to discriminate, identify and screen substances causing apoptosis in myeloid cells by utilizing cells expressing IAP as an antigen recognized by said BMAP-1 antibody specifically.

As described above, the present inventor has made it clear that the antigen recognized by the BMAP-1 antibody is identical with IAP, and that IAP has a function related to apoptosis, and has established, according to the above information, a method of screening substances causing apoptosis in myeloid cells simply and efficiently by employing cells transfected with IAP genes or cells expressing IAP.

By utilizing the apoptosis action of the substances such as monoclonal antibody obtained by the method according to the present invention, fragments thereof and substances causing apoptosis possessing binding potency to IAP to myeloid cells, since it can be thought that the substances like said monoclonal antibody and the like can kill myelocytic leukaemia cells which are thought to express antigens thereof remarkably, the substances such as said monoclonal antibody causing apoptosis in myeloid cells and fragments thereof are useful as the effective components of medical compositions such as anticancer agents and medicines for myelocytic leukemia and the like.

The method according to the present invention has been described specifically according to Examples; though as substances causing apoptosis according to the present invention are mentioned those exemplified as specific examples and typical ones, they are not always restricted thereto; it goes without saying that all the substances possessing the same characteristics and functions prepared in the same manner are included.

INDUSTRIAL APPLICABILITY

The present invention makes it possible to discriminate, identify and screen substances such as antibodies and the like causing apoptosis in myeloid cells simply and efficiently by employing cells expressing IAP and utilizing the specific binding reaction thereof. The substances possessing property of causing apoptosis in myeloid cells obtained by the method according to the present invention can be used by virtue of their characteristics as the effective components of anticancer agents and medical compositions such as medicines for myelocytic leukemia and the like useful in the field of the remedies of myelocytic leukemia and the like.

Indications relating to a Deposited Microorganism

Name and Address of Depositary Institution: National Institute of Bioscience and Human Technology, Agency of industrial Science and Technology, Ministry of Trade and Industry in Japan (address: 1–3, Higashi 1-chome, Tsukuba-shi, Ibaraki 305, Japan (Postal code 350)

Date of Deposite: Aug. 8, 1993

Accession Number: FERM BP-4382

Indication of microorganism: BMAP-1 (rat mouse hybridoma)

What is claimed is:

1. A method of screening for a substance which binds to Integrin Associated Protein (IAP) comprising contacting cells expressing IAP and cells which do not express IAP as a control with a sample containing the substance to be screened; and identifying the substance which causes apoptosis in the cells expressing IAP and which does not cause apoptosis on the cells which do not express IAP as a substance which binds IAP.

2. The method of claim 1, wherein said substance is an antibody or a F(ab)$_2$ fragment thereof.

3. The method of claim 1, wherein the cell expressing IAP is a myeloid cell.

4. The method of claim 1, wherein the cells expressing IAP are recombinant cells transfected with an IAP gene.

5. A method of screening a substance for binding to Integrin Associated Protein (IAP) comprising contacting cells expressing IAP and cells which do not express IAP as a control with a solution comprising a substance which binds to IAP and substances which do not bind to IAP; and identifying the substance which causes apoptosis in the cells expressing IAP and which does not cause apoptosis in the cells which do not express IAP as a substance which binds IAP.

6. The method of claim 5, wherein said substance is an antibody or a F(ab)$_2$ fragment thereof.

7. The method of claim 5, wherein said substance is an antibody.

8. The method of claim 5, wherein the cells expressing IAP are recombinant cells transfected with an IAP gene.

9. A method of screening for a substance which binds to Integrin Associated Protein (IAP) and which causes apoptosis of cells comprising contacting cells expressing IAP and cells which do not express IAP as a control with a sample containing the substance to be screened; and identifying the substance which causes apoptosis in the cells expressing IAP and which does not cause apoptosis on the cells which do not express IAP as a substance which binds IAP.

10. The method of claim 9, wherein said substance is an antibody or a F(ab)$_2$ fragment thereof.

11. The method of claim 9, wherein the cell expressing IAP is a myeloid cell.

12. The method of claim 9, wherein the cells expressing IAP are recombinant cells transfected with an IAP gene.

* * * * *